(12) United States Patent
Tseng et al.

(10) Patent No.: US 8,219,205 B2
(45) Date of Patent: Jul. 10, 2012

(54) FLEXIBLE ANTENNA MODULE FOR WIRELESS ENERGY TRANSMISSION

(75) Inventors: Kuo-Hua Tseng, Hsinchu (TW);
Pin-Hsun Huang, Hsinchu (TW);
Yu-Kon Chou, Hsinchu (TW); Pei-Ying Shieh, Hsinchu (TW); Tsung-Ter Kuo, Hsinchu (TW); Wen-Yang Chou, Hsinchu (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 0 days.

(21) Appl. No.: 13/014,078

(22) Filed: Jan. 26, 2011

(65) Prior Publication Data
US 2011/0137380 A1 Jun. 9, 2011

Related U.S. Application Data

(63) Continuation of application No. 11/403,820, filed on Apr. 14, 2006, now abandoned.

(30) Foreign Application Priority Data

Feb. 9, 2006 (TW) .............................. 95104327 A (51) Int. Cl.
*A61N 1/00* (2006.01)
*A61B 5/02* (2006.01)

(52) U.S. Cl. .............................. 607/60; 607/61; 600/486

(58) Field of Classification Search .............. 607/60–61; 600/486
See application file for complete search history.

(56) References Cited

U.S. PATENT DOCUMENTS

| | | | |
|---|---|---|---|
| 5,165,284 A | | 11/1992 | Shoji et al. |
| 5,383,912 A | | 1/1995 | Cox et al. |
| 5,545,191 A | | 8/1996 | Mann et al. |
| 6,333,712 B1* | | 12/2001 | Haugse et al. ................ 342/375 |
| 6,636,769 B2 | | 10/2003 | Govari et al. |
| 6,638,231 B2 | | 10/2003 | Govari et al. |
| 6,658,300 B2 | | 12/2003 | Govari et al. |
| 6,903,704 B2 | | 6/2005 | Forster et al. |
| 2002/0077553 A1 | | 6/2002 | Govari et al. |
| 2006/0047327 A1* | | 3/2006 | Colvin et al. ................... 607/60 |

FOREIGN PATENT DOCUMENTS

JP 06270243 9/1994

* cited by examiner

*Primary Examiner* — Nicole F Lavert
(74) *Attorney, Agent, or Firm* — Bacon & Thomas, PLLC (57) ABSTRACT

This invention provides a flexible antenna module for wireless energy transmission, which uses an antenna size controlling device to adjust the antenna's size to conform a living body's outer portion wearing the flexible annular antenna. An antenna energy transmission control module is provided to adjust the power for driving the flexible annular antenna according to the deformation of the flexible annular antenna. This invention can adjust both the antenna size to fit the individual and the power for driving the antenna. The individual can use the present antenna module under a comfortable, safe and reliable circumstance.

3 Claims, 6 Drawing Sheets

FLEXIBLE ANTENNA MODULE FOR WIRELESS ENERGY TRANSMISSION

This application is a continuation of U.S. patent application Ser. No. 11/403,820 (abandoned), which was filed on Apr. 14, 2006, and published as U.S. Patent Publication No. 2007/0185546, and which is incorporated by reference herein.

BACKGROUND OF THE INVENTION

1. Field of the Invention

The present invention relates to a flexible antenna module for wireless energy transmission; and more particularly to a flexible antenna module for wireless energy transmission, which enables the antenna's size adjustable to conform an individual's outer portion.

2. Description of the Related Art

Electrical stimulator combines the principles of Chinese traditional Point Percussion Therapy and western TENS (Transcutaneous Electrical Nerve Stimulation). The stimulator uses micro electric current to stimulate specific acupuncture points to achieve the health care effect. That is it can stimulate the self-cure mechanism of the body with an electric current having suitable intensity and frequency continuously, gently stimulating the nerve, the muscle and the cell. On clinical uses, the method of treatment is divided into the Transcutaneous Electrical Nerve Stimulation (TENS) and the Electrical Muscle Stimulation (EMS).

The electrical stimulation has been widely utilized for the function of recovery. Recently, as a result of the breakthrough of the micro electron technology, the micro mechanical and electrical technology, the biological material and the biological compatible seal technology, the electrical stimulator tends to have a small and implanted form.

Figure 1:
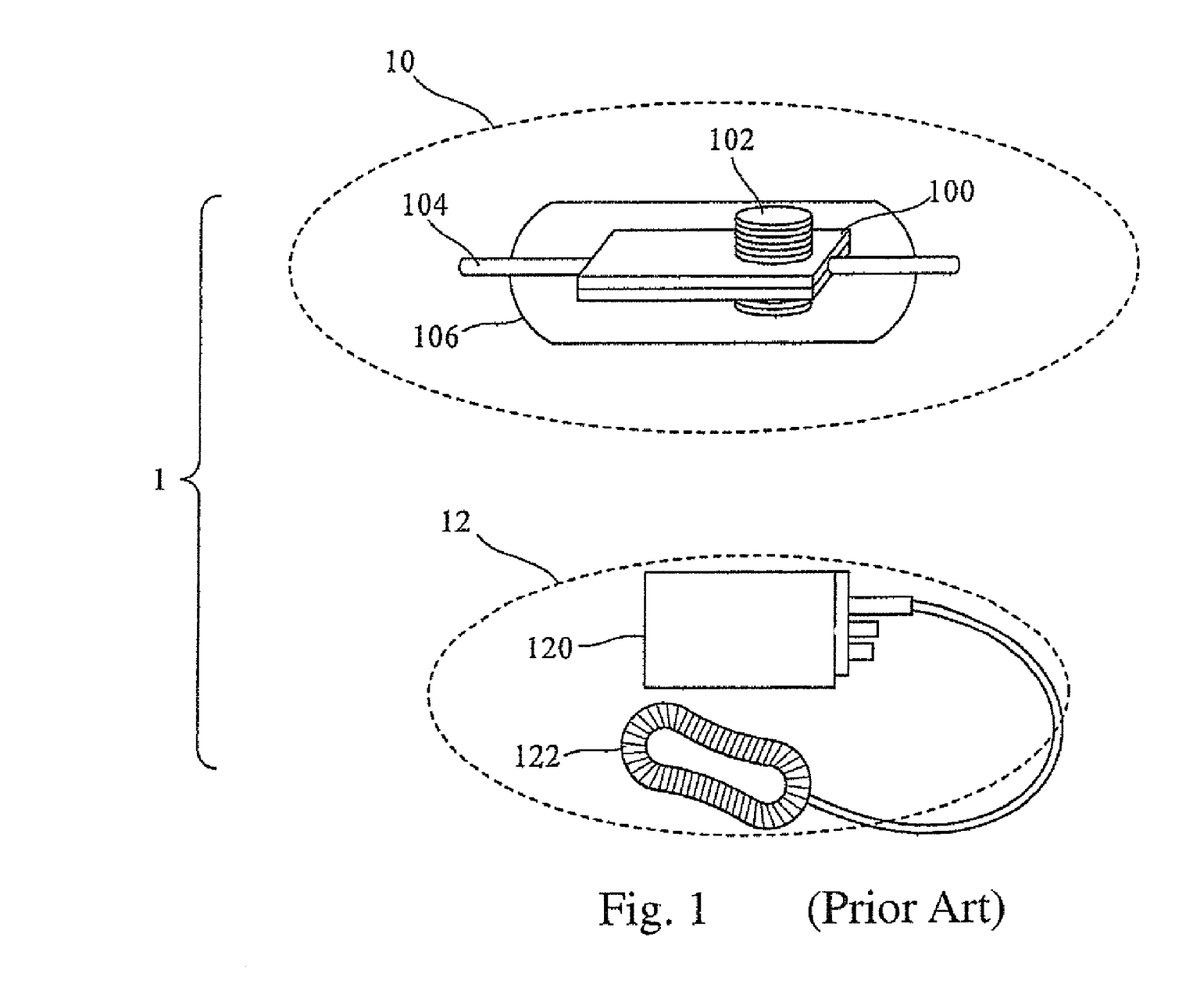
FIG. 1 is a schematic view of an assembly of a conventional implanted electrical stimulating device.

FIG. 1 is a conventional implanted electrical stimulator comprising an in vivo electrical stimulating module 10 and an in vitro energy-transmitting module 12. The in vivo electrical stimulating module 10 includes a circuit board 100; an in vivo energy-transmitting coil 102 and a pair of positive/negative electrodes 104 provided on the circuit board 100 and a biological compatible polymer layer 106 covering the whole in vivo electrical stimulating module 10. The in vitro energy-transmitting module 12 includes an in vitro control module 120 and an in vitro energy-transmitting coil 122. The in vitro control module 120 will drive the in vitro energy-transmitting coil 122 to emit wireless energy. The wireless energy will be received by the in vivo energy-transmitting coil 102 and converted by the circuit board 100 into a voltage source. The converted voltage source will be applied on the positive/negative electrodes 104 to generate an electrical stimulating current.

As mentioned above, the conventional implanted electrical stimulator transmits the energy from an external antenna module to an in vivo implanted electrical stimulating element via radio frequency (RF) and receive the energy by an internal electronic component to automatically generate an electrical stimulation, rather than stimulating the nervous muscle with an electrical line penetrating through the skin, thus can reduce the probability of wound infection. However, the energy needed by the implanted electrical stimulating device is unidirectionally transmitted into the implanted electrical stimulating device via a fixed-size antenna. That is, the energy is transmitted to the in vivo electrical stimulating module via an external energy-transmitting antenna to stimulate the nervous muscle. In operation, this energy-transmitting method may suffer from the displacement of the implanted electrical stimulating element or the electromagnetic interference from surrounding environment and thus change the properties of the energy-transmitting circuit, thereby causing to transmit excessive energy to result in heat-generating from the implanted electrical stimulating element, or causing to transmit too little energy to result in abnormal operation or even malfunction, thereby further causing unnecessary damage to the human body. In addition, effective detection of the position of the implanted electrical stimulating element and provision of effective energy-transmission are also general issues encountered for the implanted electrical stimulators.

In brief, the method for energy transmission of the conventional implanted electrical stimulator has the following disadvantages:

1. The antenna's size is fixed, and unsafe and un-comfortable in utilization.
2. The exact position of the implanted electrical stimulator is not easy to detect.
3. Control of the power transmission does not come easy.
4. Properties of the energy transmission circuit easily suffer from electromagnetic interference from surrounding environment.

Accordingly, there is an improved antenna technique for energy transmission provided.

SUMMARY OF THE INVENTION

The primary object of the present invention is to provide a flexible antenna module for wireless energy transmission, in which a flexible antenna's size is adjustable to fit the individual body's portion and provided for the individual to use under safe and comfortable circumstance.

Another object of the present invention is to provide a flexible antenna module for wireless energy transmission, which can control the antenna's size and adjust a driving power of the antenna depending on the deformation of the antenna so as to increase the energy-transmitting reliability and safety of the flexible antenna module for wireless energy transmission.

Further object of the present invention is to provide a flexible antenna module for wireless energy transmission, which uses wireless feedback control to optimize wireless energy transmission such that the implanted element can exactly and effectively stimulate the nerve and muscle.

According to the above objects of the present invention, the present invention provides a flexible antenna module for wireless energy transmission, which comprises a flexible annular antenna, a pressure sensor and an antenna size controlling device. The flexible annular antenna is provided on a living body's outer portion. The pressure sensor is provided on an inner side of the flexible annular antenna to detect a pressure value generated from touching the living body's outer portion by the flexible annular antenna. The antenna size controlling device is provided to control the size of the flexible annular antenna. The antenna size controlling device fixes the size of the flexible annular antenna when the pressure value detected by the pressure sensor is up to a threshold value.

By the flexible antenna device for energy transmission, a flexible antenna's size is adjustable to fit the individual such that the individual can use the flexible antenna device under safe and comfortable circumstance.

In one another aspect, the present invention provides a flexible antenna energy transmission controlling module combined with the flexible antenna device for energy transmission. The flexible antenna energy transmission controlling module comprises an antenna deformation detector and an antenna deformation compensation circuit. The antenna deformation detector is used to detect the deformation of the flexible annular antenna, and the antenna deformation compensation circuit depends on the deformation of the flexible antenna to adjust an output power for driving the flexible annular antenna. By the flexible antenna energy transmission controlling module the effectiveness, reliability and safety of the flexible antenna for energy transmission are increased.

DETAILED DESCRIPTION OF THE PREFERRED EMBODIMENTS

The present invention provides a flexible antenna device for energy transmission and an energy transmission controlling module thereof. The present invention adopts an antenna size controlling device to adjust the size of the flexible annular antenna to conform a living body's outer portion so as to increase the comfort and convenience of the flexible annular antenna in utilization. Further, the present flexible antenna device for energy transmission is combined with an energy transmission controlling module, and by the energy transmission controlling module the deformation of the flexible annular antenna after the size adjustment is detected. An output power for driving the flexible annular antenna is compensated depending on the deformation of the flexible annular antenna. As such, the flexible annular antenna is able to emit exact energy to make an implanted element in vivo effectively and safely stimulate the nerve and muscle. On the other side, the flexible antenna device for energy transmission and the energy transmission controlling module of the present invention can be equipped with a wireless feedback control module to provide an optimum energy to the implanted element. As such, the implanted element can exactly and effectively stimulate the nerve and muscle. Besides, the wireless feedback control module is provided to have a design for overload proof to avoid the error action of the implanted element to induce damages on living body.

The objects and advantages of the present invention will become clearer understood by the following detailed description of the embodiments with reference to accompanying drawings.

Figure 2A:
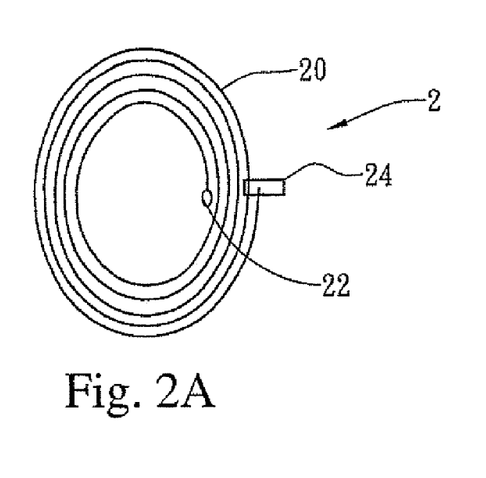
FIG. 2A shows a schematic top view of a flexible antenna device for energy transmission according to one embodiment of the present invention.
Figure 2B:
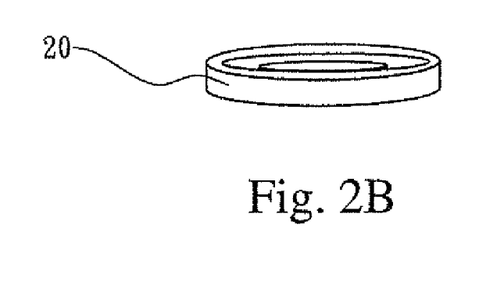
FIG. 2B shows a schematic side view of the flexible antenna device for energy transmission of FIG. 2A.
Figure 3A:
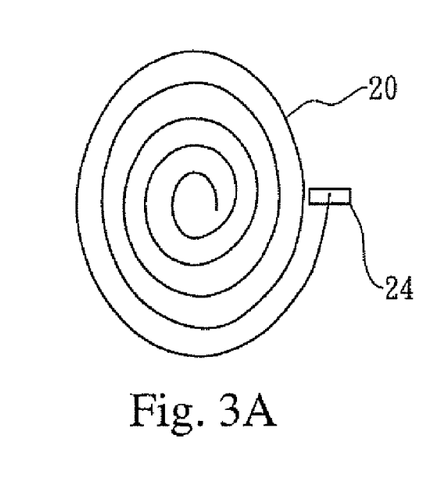
FIG. 3A to FIG. 3C is schematic views showing deformation processes of the flexible antenna device for energy transmission of FIG. 2.
Figure 3B:
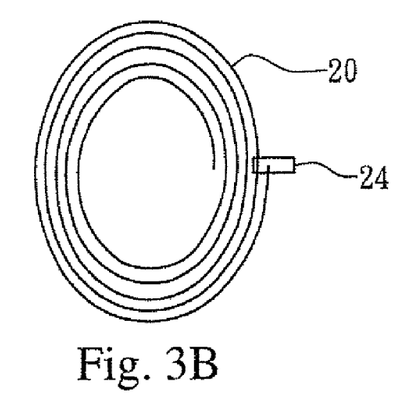
Figure 3C:
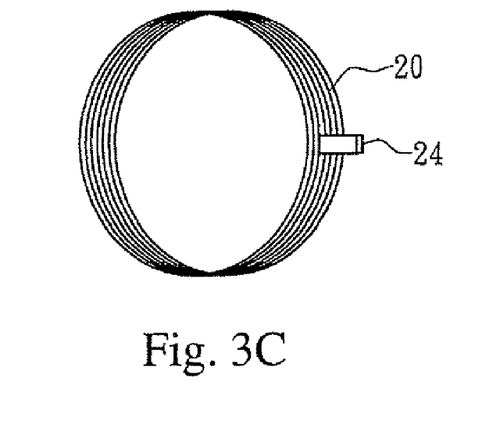
Figure 4A:
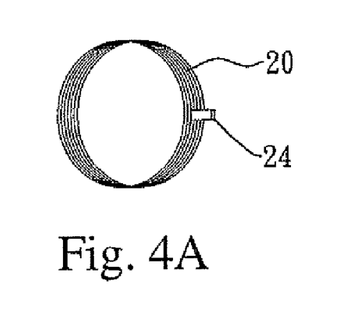
FIG. 4A to FIG. 4C shows schematic views of the present flexible antenna device for energy transmission in different sizes.
Figure 4B:
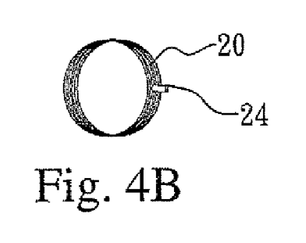
Figure 4C:
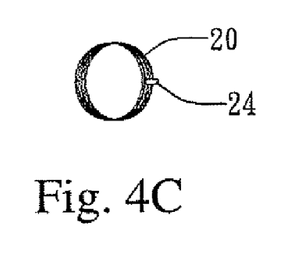

FIG. 2A shows a schematic top view of a flexible antenna device for energy transmission according to one embodiment of the present invention. FIG. 2B shows a schematic side view of the flexible antenna device for energy transmission of FIG. 2A. In this embodiment, the flexible antenna device for energy transmission 2 of the present invention comprises a flexible annular antenna 20, a pressure sensor 22 and an antenna size controlling device 24. The flexible annular antenna 20 is provided on a living body's outer portion. The pressure sensor 22 is provided on an inner side of the flexible annular antenna 20 to detect a pressure value generated from touching the flexible annular antenna 20 by the living body's outer portion. The antenna size controlling device 24 is provided to control the size of the flexible annular antenna 20. The flexible annular antenna is multi-concentric annular shaped, and the antenna size controlling device 24 can adjust the multi-concentric annular antenna 20, referring to FIG. 3A to FIG. 3C. In other words, the size of the flexible annular antenna 20 is adjustable to fit the individual, referring to FIG. 4A to FIG. 4C, such that the individual can comfortably wear the flexible annular antenna 20. In practice use, the antenna size controlling device 24 automatically adjusts the size of the flexible annular antenna 20 until a pressure value applied to the living body's outer portion by the flexible annular antenna 20 is up to a threshold value and detected by the pressure sensor 22. Then, the size of the flexible antenna 20 is fixed by the antenna size controlling device 24 to conform the individual's outer portion.

Figure 5:
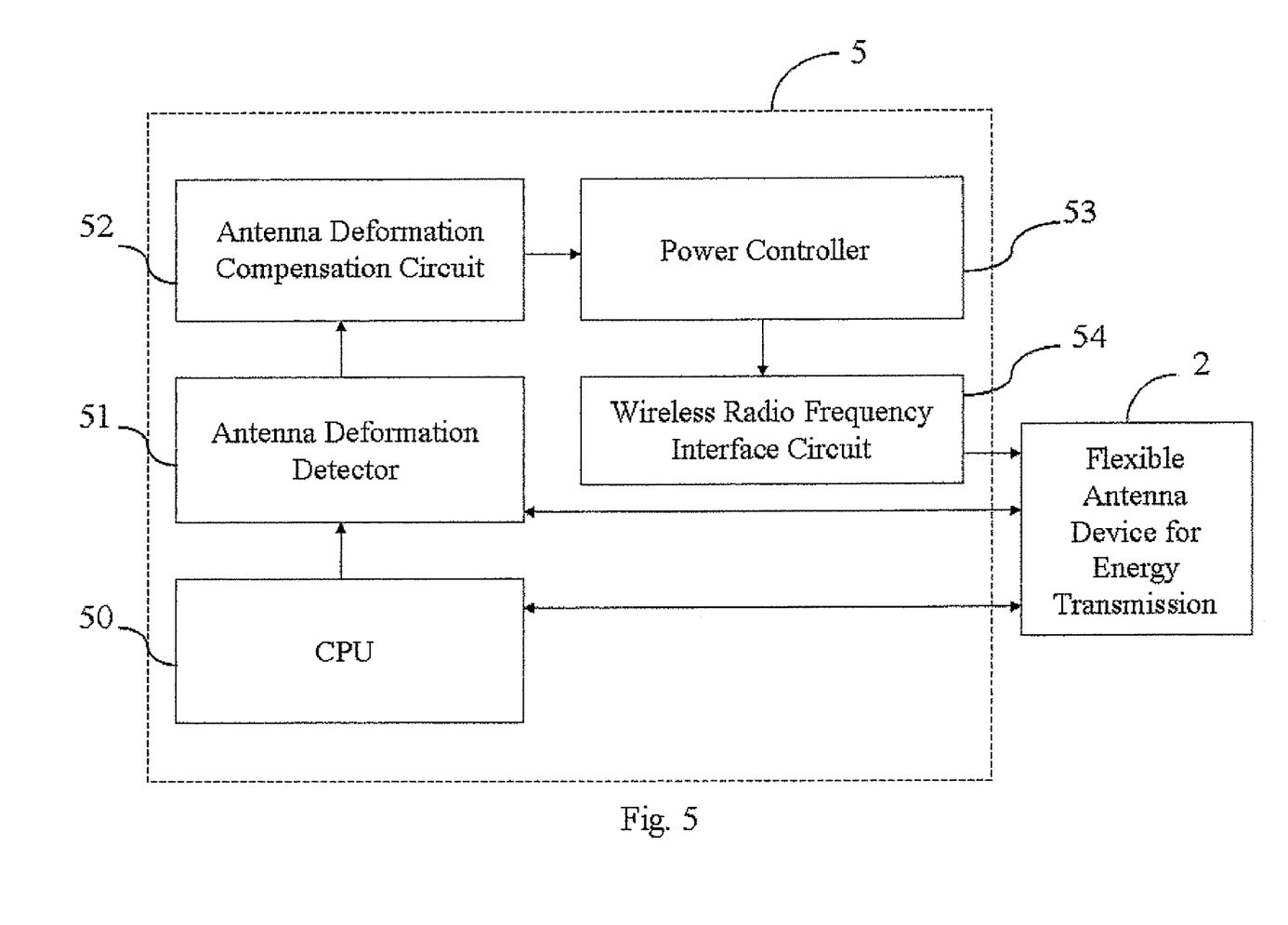
FIG. 5 is a functional block diagram of a flexible antenna energy transmission module for wireless energy transmission according to one embodiment of the present invention.

On the other side, the flexible antenna device for energy transmission 2 of the present invention can be combined with a flexible antenna energy transmission controlling module 5, referring to FIG. 5, so that the emitting energy of the flexible antenna device for energy transmission 2 is not influenced by different deformations of the flexible annular antenna 20 causing by different individuals or different body's portions wearing the flexible annular antenna 20. In other words, the flexible antenna energy transmission controlling module 5 can depend on the deformation of the flexible annular antenna 20 after the size adjustment to adjust an output power for driving the flexible annular antenna 20. As such, the emitting energy of the flexible annular antenna 20 is not influenced by the deformations of the flexible annular antenna 20. The flexible antenna energy transmission controlling module 5 comprises a central processing unit (CPU) 50, an antenna deformation detector 51, an antenna deformation compensation circuit 52, a power controller 53 and a wireless radio frequency interface circuit 54. The flexible annular antenna 20 is provided on a living body's outer portion, and the size of the flexible annular antenna 20 is adjusted by the antenna size controlling device 24. A pressure value which is applied to the living body's outer portion by the flexible annular antenna 20 is detected by the pressure sensor 22 and transmitted to CPU 50 to determine whether the pressure value is up to the threshold value. When the pressure value is up to the threshold value, the antenna size controlling device 24 is controlled by CPU 50 to fix the size of the flexible annular antenna 20, and the deformation of the flexible annular antenna 20 is detected by the antenna deformation device 51. In the present invention, the antenna deformation detector 51 can detect the deformation of the flexible annular antenna 20 by way of voltage division or current division with passive components. Alternatively, the antenna deformation detector 51 can detect the deformation of the flexible annular antenna 20 by an electric field or magnetic field sensing element. The antenna deformation compensation circuit 52 depends on the deformation of the flexible annular antenna 20 detected by the antenna deformation detector 51 to determine the power compensation value for driving the flexible annular antenna 20, and transmitting to the power controller 53. Depending on the power compensation value, the power controller 53 outputs a compensated driving power to the wireless radio frequency interface circuit 54, and converting to wireless electrical waves for transmission via the flexible annular antenna 20.

On the other side, the flexible antenna device for energy transmission 2 and the flexible antenna energy transmission controlling module 5 of the present invention can be applied to one implanted electrical stimulating system, and a wireless feedback control module for optimizing transmitting energy and transmitting position can be equipped with to provide an optimizing electrical stimulating energy for an implanted electrical stimulating element. As such, the implanted electrical stimulating element can perform exact and effective stimulating action to the nerve and muscle.

Figure 6:
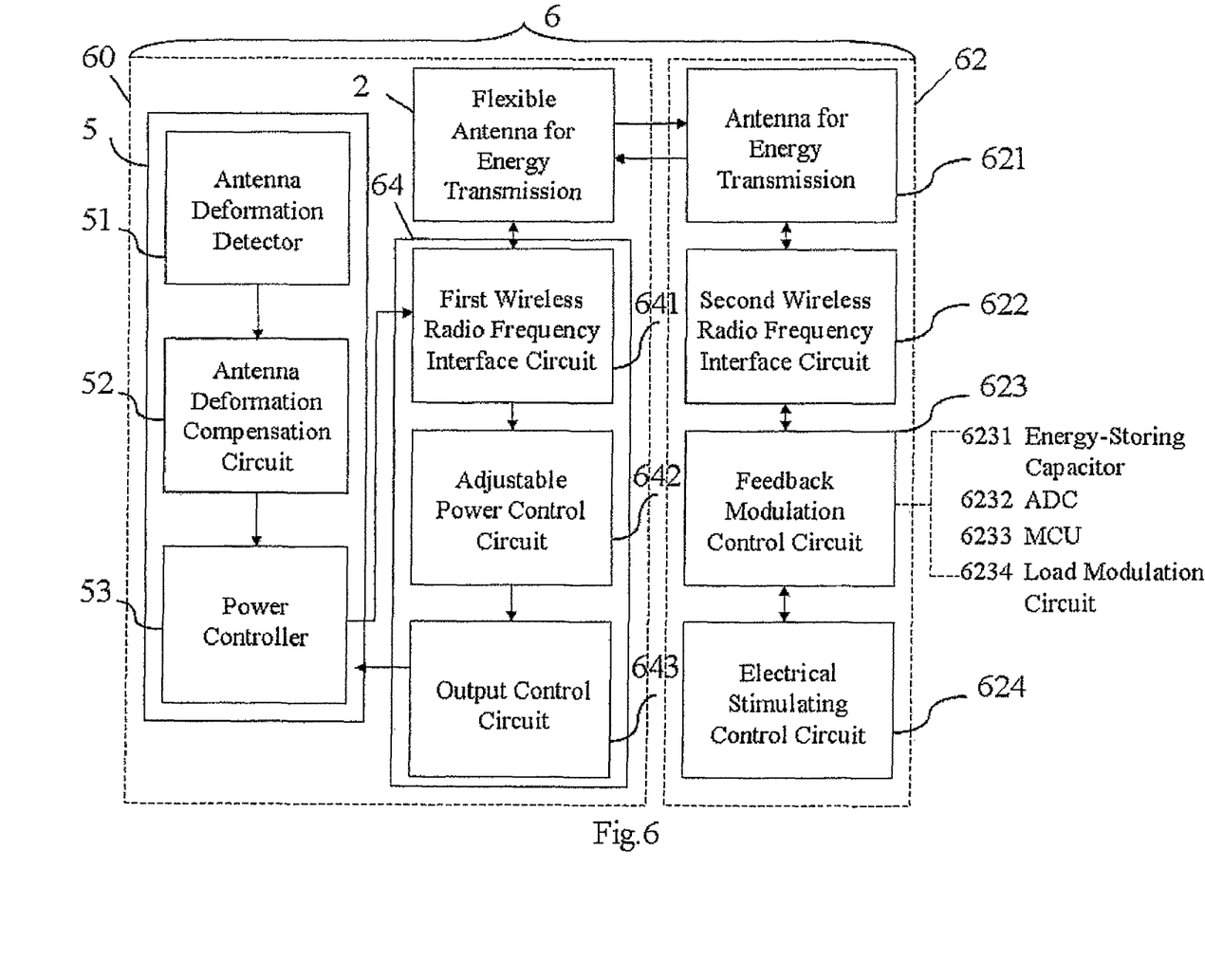
FIG. 6 is a functional block diagram of an implanted electrical stimulating system of the present invention.
Figure 7:
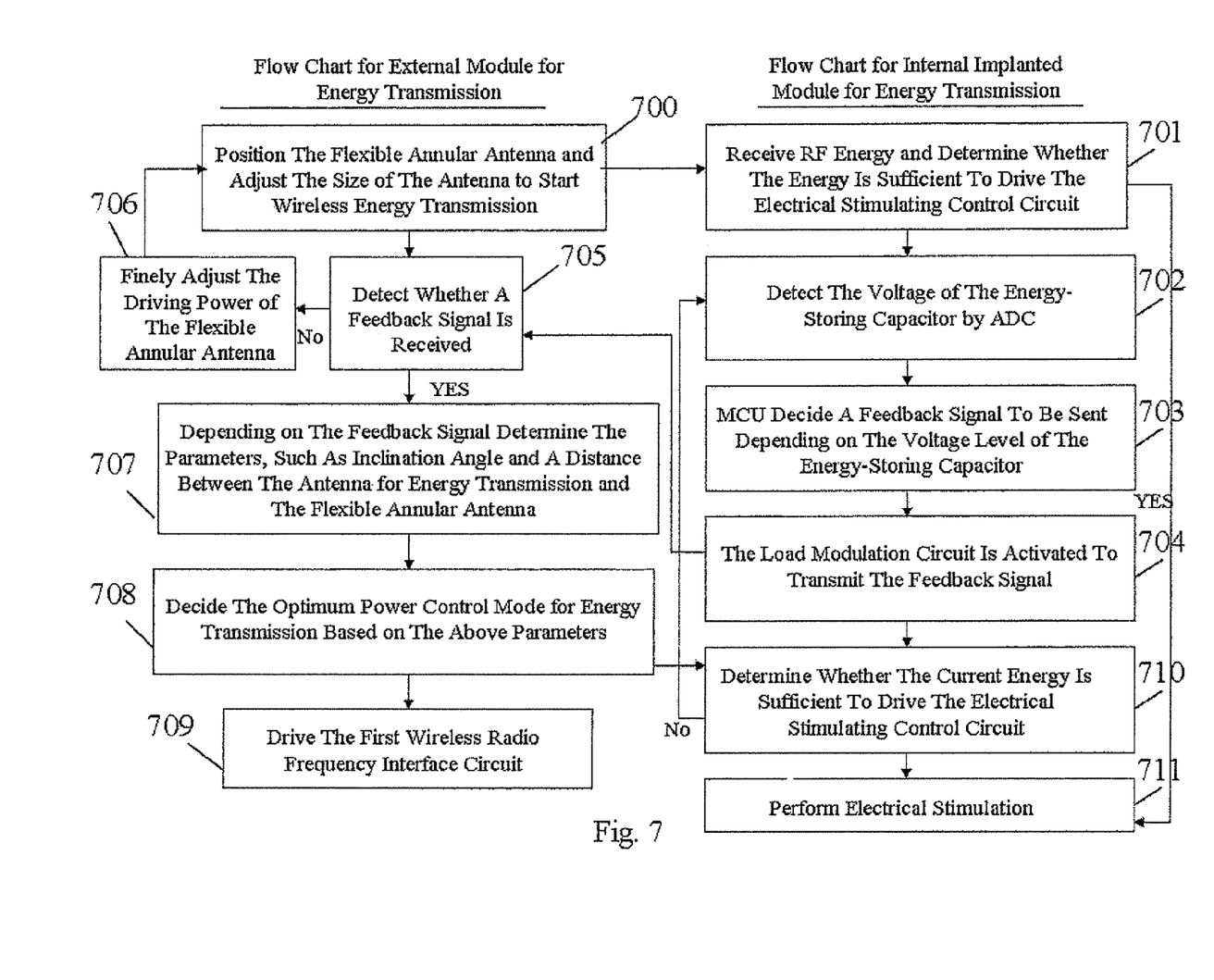
FIG. 7 is a flow chart of the implanted electrical stimulating system of FIG. 6.

FIG. 6 is a functional block diagram of the implanted electrical stimulating system 6 in which the flexible antenna device for energy transmission 2 and the flexible antenna energy transmission controlling module 5 of the present invention are applied. FIG. 7 is a flow chart of the implanted electrical stimulating system 6. The implanted stimulating system 6 comprises an external module for energy transmission 60 and an internal implanted module 62. The external module for energy transmission 60 is provided on a living body's outer portion and comprises the flexible antenna device for energy transmission 2, the flexible antenna energy transmission controlling module 5 and an electrical stimulating signal control module 64. The flexible antenna device for energy transmission 2 comprises the flexible annular antenna 20, the pressure sensor 22 and the antenna size controlling device 24, referring to FIG. 2A. The flexible antenna energy transmission controlling module 5 comprises the antenna deformation detector 51, the antenna deformation compensation circuit 52 and the power controller 53. The electrical stimulating signal control module 64 comprises a first wireless radio frequency interface circuit 641, an adjustable power control circuit 642 and an output control circuit 643. The flexible annular antenna 20, which is deformed to conform a living body's outer portion, is provided to wirelessly transmit energy. The antenna deformation detector 51 is used to detect the deformation of the flexible annular antenna 20. The antenna deformation compensation circuit 52 depends on the deformation of the flexible annular antenna 20 to provide a compensation power to the power controller 53. The first wireless radio frequency interface circuit 641 is used to drive the flexible annular antenna 20 to emit energy and convert a sense signal received by the flexible annular antenna 20 into a first electronic signal. The adjustable power control circuit 642 depends on the first electronic signal to determine the optimum power control mode for energy transmission. The output control circuit 643 depends on the optimum power control mode for energy transmission to send an output power to the power controller 53. The power controller 53 depends on the compensation power to adjust the output power to obtain a compensated output power, and transmitting to the first wireless radio frequency interface circuit 641 to drive the flexible annular antenna 20 to emit energy. The internal implanted module 62 is implanted into the living body and comprises an antenna for energy transmission 621, a second wireless radio frequency interface circuit 622, a feedback modulation control circuit 623 and an electrical stimulating control circuit 624. The feedback modulation control circuit 623 has an energy-storing capacitor 6231, an ADC (Analog-to-Digital Converter) 6232, a MCU (Micro Central Unit) 6233 and a load modulation circuit 6234. The antenna for energy transmission 621 receives the energy emitted by the flexible annular antenna 20. The second wireless radio frequency interface circuit 622 converts the energy into a second electronic signal and then sends the second electronic signal to the feedback modulation control circuit 623. The MCU 6233 depends on the second electronic signal to determine whether to drive electrical stimulating control circuit 624. If the result is yes, then starting up the electrical stimulating process. Otherwise, it depends on the second electronic signal to generate a feedback signal for transmission via the antenna for energy transmission 621. Then the feedback signal is received by the flexible annular antenna 20 to form the sense signal. When the flexible annular antenna 20 detects no feedback signal, the driving power of the flexible annular antenna 20 is fine-tuned until the feedback signal is detected.

Referring to FIG. 6 and FIG. 7, the working principle and flow chart of the implanted electrical stimulating system 6 is described in detail as follows.

First, in step 700, the flexible annular antenna 20 is provided on a living body's outer portion, and the size of the flexible annular antenna 20 is adjusted to conform the living body's outer portion. The flexible antenna energy transmission control module 5 detects the deformation of the flexible annular antenna 20 and depends on the deformation of the flexible annular antenna 20 to output a compensated driving power to the first wireless radio frequency interface circuit 641 to activate the external module for energy transmission 60 for wireless energy transmission. Next, in step 701, the wireless radio frequency energy is received by the antenna for energy transmission 621 of the internal implanted module 62, and the wireless radio frequency energy is converted to the second electronic signal by the second wireless radio frequency interface circuit 622, and transmitting to the feedback modulation control circuit 623. The MPU 6233 depends on the second electronic signal to determine whether the energy is sufficient to activate the electrical stimulating control circuit 624. If the result is yes, go to step 711, activating the electrical stimulating control circuit 624 to start up the electrical stimulating. Otherwise, go to step 702, the ADC 6232 of the feedback modulation control circuit 623 detects the voltage level of the energy-storing capacitor 6231. Next, in step 703, the MCU 6233 of the feedback modulation control circuit 623 determines the feedback signal to be sent depending on the voltage level of the energy-storing capacitor 6231. Then, in step 704, the load modulation circuit 6234 of the feedback modulation control circuit 623 is activated to transmit the feedback signal. Next, in step 705, the external module for energy transmission 60 detects the feedback signal by the flexible annular antenna 20. When the flexible annular antenna 20 detects no feedback signal, go to step 706, the driving power of the flexible annular antenna 20 is fine-tuned, then steps 700 to 705 are repeated, until the flexible annular antenna 20 detects the feedback signal. When the flexible annular antenna 20 detects the feedback signal, go to step 707, the feedback signal is converted to the first electronic signal by the first wireless radio frequency interface circuit 641, and the first electronic signal is sent to the adjustable power control circuit 642. The adjustable power control circuit 642 depends on the first electronic signal to determine the inclination angle and the distance between the antenna for energy transmission 621 and the flexible annular antenna 20. In step 708, the adjustable power control circuit 642 depends on the aforesaid parameters to determine the optimum power control mode for energy transmission. Next, in step 709, the output control circuit 643, such as a digital control circuit, depends on the optimum power control mode for energy transmission to send an output power to the power controller 53. The power controller 53 depends on the compensation power provided by the antenna deformation compensation circuit 52 to output a compensated driving power to the first wireless radio frequency interface circuit 641 to drive the flexible annular antenna 20 for wireless energy transmission. Next, go to step 701, the energy is received by the second wireless radio frequency interface circuit 622 to convert to the second electronic signal, and depending on the second electronic signal determines whether the energy is sufficient to activate the electrical stimulating control circuit 624. If the result is yes, go to step 711, activating the electrical stimulating control circuit 624, and starting up the electrical stimulating. Otherwise, go to step 702 to 709, until the electrical stimulating control circuit 624 is activated.

As mentioned above, there are many advantages for the implanted electrical stimulating system 6 of the present invention:

1. The size of the flexible annular antenna 20 can be adjusted by the antenna size controlling device 24 to conform a living body's portion so as to increase the comfort in utilization; and utilizing the flexible antenna energy transmission control module 5 to compensate the variation of emitting energy of the flexible antenna after deformation facilitates the flexible antenna to emit exact energy.

2. The flexible antenna module for energy transmission 60 adopts an external wireless feedback control to provide an optimum electrical stimulating energy for an implanted element so that the implanted element can effectively and safely perform the electrical stimulating action to the nerve and muscle.

3. The design of overload proof can avoid the error action of the implanted element to make individual damage, and increasing the safety of product in utilization.

4. In the future, the implanted electrical stimulating system 6 can combine with a feedback monitor device to provide physiological related information for doctors to accomplish a specialized design for stimulating signals to increase the benefit in medical use.

The above specific embodiments are only illustrative and does not intend limiting the scope of the present invention. And many variations can be introduced on these embodiments without departing from the spirit of the disclosure or from the scope of the appended claims.

What is claimed is:

1. A device for optimizing energy transmission for an implanted device, comprising:

an external module for energy transmission adapted to be provided on a living body's outer portion and comprising a flexible annular antenna adapted to be provided on the living body's outer portion, a pressure sensor provided at an inner side of said flexible annular antenna for detecting a pressure value generated from said pressure sensor when the pressure sensor is touched by the living body's outer portion, an antenna size controlling device for controlling a size of said flexible annular antenna, a flexible antenna energy transmission controlling module and an electrical stimulating signal control module; wherein said flexible antenna energy transmission controlling module comprises an antenna deformation detector, an antenna deformation compensation circuit and a power controller, said electrical stimulating signal control module comprises a first wireless radio frequency interface circuit, an adjustable power control circuit and an output control circuit; wherein said flexible annular antenna is used to perform wireless energy transmission and deformed to conform the living body's outer portion until said pressure value detected by said pressure sensor is up to a threshold value, and then said antenna size controlling device fixes the size of said flexible annular antenna, said antenna deformation detector is provided to detect the deformation of said flexible annular antenna and said antenna deformation compensation circuit is provided to apply a compensation power to said power controller depending on the deformation of the flexible annular antenna, said first wireless radio frequency interface circuit is used to drive said flexible annular antenna to emit energy and convert a sense signal received by said flexible annular antenna into a first electronic signal, said adjustable power control circuit determines an optimum power control mode for energy transmission depending on said first electronic signal, said output control circuit sends an output power to said power controller depending on the optimum power control mode for energy transmission, said power controller adjusts the output power to obtain a compensated output power depending on the compensation power, and transmitting the compensated output power to said first wireless radio frequency interface circuit in order to drive said flexible annular antenna to emit energy; and an internal implanted module implanted inside the living body and comprising an energy transmission antenna, a second wireless radio frequency interface circuit, a feedback modulation control circuit and an electrical stimulating control circuit, wherein said energy transmission antenna receives the energy emitted by said flexible annular antenna, said second wireless radio frequency interface circuit converts the received energy into a second electronic signal and then sends said second electronic signal to said feedback modulation control circuit, said feedback modulation control circuit depends on said second electronic signal to determine whether to drive electrical stimulating control circuit or generate a feedback signal to electrical stimulating signal control module;

wherein said adjustable power control circuit depends on said feedback signal to determine an inclination angle and a distance of said energy transmission antenna and said flexible annular antenna in order to determine said optimum power control mode for energy transmission.

2. The device for optimizing energy transmission for an implanted device of claim 1, wherein said output control circuit is a digital control circuit.

3. The device for optimizing energy transmission for an implanted device of claim 1, wherein said feedback modulation control circuit has an energy-storing capacitor, an ADC (Analog-to-Digital Converter), a MCU (Micro Central Unit) and a load modulation circuit, wherein said energy-storing capacitor converts said second electronic signal into a voltage level, said ADC detects said voltage level, said MCU depends on said voltage level to determine said feedback signal to be transmitted, and said load modulation circuit is activated to transmit said feedback signal.

* * * * *